(12) United States Patent
Beck et al.

(10) Patent No.: US 6,471,514 B2
(45) Date of Patent: Oct. 29, 2002

(54) ERGONOMIC GRIP FOR HAND INSTRUMENTS

(75) Inventors: Melanie L. Beck, Olathe, KS (US); Theresa A. Forgy, Olathe, KS (US)

(73) Assignee: Acushy Product Co., L.L.C., Olathe, KS (US)

( * ) Notice: Subject to any disclaimer, the term of this patent is extended or adjusted under 35 U.S.C. 154(b) by 0 days.

(21) Appl. No.: 09/792,353

(22) Filed: Feb. 23, 2001

(65) Prior Publication Data

US 2002/0119422 A1 Aug. 29, 2002

(51) Int. Cl.$^7$ ................................................ A61C 3/00
(52) U.S. Cl. ...................................................... 433/141
(58) Field of Search ................................ 433/141, 142, 433/144; 81/177.1

(56) References Cited

U.S. PATENT DOCUMENTS

| | | | |
|---|---|---|---|
| 4,098,506 A | | 7/1978 | Gaiser |
| 4,283,808 A | | 8/1981 | Beebe |
| 4,712,304 A | | 12/1987 | Sanelli |
| 5,090,907 A | * | 2/1992 | Hewitt et al. ............... 433/141 |
| 5,305,490 A | | 4/1994 | Lundgren |
| 5,398,369 A | | 3/1995 | Heinzelman et al. |
| 5,501,597 A | * | 3/1996 | Wilson ........................ 433/141 |
| 5,781,958 A | * | 7/1998 | Messmann et al. ......... 433/141 |
| 5,926,901 A | | 7/1999 | Tseng et al. |
| 6,049,936 A | | 4/2000 | Holley |
| 6,234,798 B1 | * | 5/2001 | Beals et al. ................. 433/216 |
| 6,305,937 B1 | * | 10/2001 | Williams ..................... 433/141 |
| 2001/0031443 A1 | * | 10/2001 | Ferranti ....................... 433/141 |

OTHER PUBLICATIONS

Dobias, Mary T., "Carpal Tunnel Syndrome: Can it Be Prevented", Dental Hygienist News, vol. 5, No. 1, Winter 1992, Harfst Assoc. Inc., Bloomfield, MI, USA.

Conrad, John C. et al., A Short–Term, Three–Year Epidemiological Study of Median Nerve Sensitivity in Practicing Dental Hygienists:, vol. 67, No. 5, Jul.–Aug. 1993, Journal of Dental Hygiene.

Akesson, Ingrid et al., "Neuropathy in female dental Personnel exposed to High Frequency Vibrations", Occupational and Environmental Medicine, vol. 52, 1995, pp. 116–123; Sweden.

Liskiewicz, Susanne Tishler et al., "Cumulative Trauma Disorders: An Ergonomic Approach for Prevention", Journal of Dental Hygiene, vol. 71, No. 4, Summer 1997, USA.

Bramson, James B. et al., "Evaluation Dental Office Ergonomic Risk Factors and Hazards", Journal of the American Dental Associatio, Feb. 1998, vol. 129, pp. 174–183.

Michalak–Turcotte, Claudia, "Controlling Dental Hygiene Work–Related Musculosketetal Disroders: The Ergonomic Process", The Journal of Dental Hygiene, vol. 74, Issue 1, Winter 2000, pp. 41–49, USA.

Stiik, Todd P., "An ANalysis of Cumulative Trauma Disorders in Dental Hygienists", The Journal of Practical Hygiene, Mar./Apr. 2000, pp. 19–25, USA.

Hand Tech 2000, LLC advertisement, modified Feb. 22, 2000.

* cited by examiner

Primary Examiner—Cary E. O'Connor
(74) Attorney, Agent, or Firm—Chase Law Firm, L.C.

(57) ABSTRACT

An ergonomic grip for an instrument or tool handle is provide which reduces upper extremity musculoskeletal disorder (MSDs) by increasing the grip cross-sectional area, reducing the grip force necessary to manipulate the instrument and increasing the grip comfort using an elastomeric gripping surface. Vibrations from the instrument or tool are reduced or eliminated to further reduce MSDs.

26 Claims, 4 Drawing Sheets

ERGONOMIC GRIP FOR HAND INSTRUMENTS

BACKGROUND OF THE INVENTION

This invention relates to an apparatus for reducing musculoskeletal disorders, and, in particular, to a gripping system for small diameter tool handles which relates repetitive motion injuries.

Musculoskeletal Disorders (MSDs) are injuries and illnesses that affect muscles, nerves, tendons, ligaments and joints. Individuals suffering from MSDs may experience loss of strength for gripping, reduced range of motion, loss of muscle function and the inability to do everyday tasks. Some of the common MSDs affecting the hands and wrists include carpal tunnel syndrome (CTS), tendinitis, lateral epicondylitis, synovitis and de Quervain's tenosynovitis. CTS is the most common compression neuropathy of the upper extremity and is predominantly occupationally related when the work environment requires repetitive hand-intensive tasks such as in the dental hygiene profession, for example. CTS has been diagnosed in more than 10% of dental hygienists with up to 65% reporting pain in the hand and wrist. CTS is a nerve entrapment disorder that affects the median nerve as it passes through the region of the wrist known as the carpal tunnel. Symptoms of CTS include paresthesias, incoordination of the involved fingers, the relatively rapid onset of hand fatigue, and in severe cases, true hand weakness. Although symptom onset is generally insidious, it can be acute and precipitated by vigorous or prolonged hand use. Similarly, 9.2% of dentists have been diagnosed by a physician as having some type of repetitive motion disorder.

According to the Occupational Safety and Health Administration (OSHA), in 1996 U.S. workers experienced more than 647,000 lost work days due to work-related MSDs (WMSDs). WMSDs now account for 34 percent of all lost work day injuries and illnesses costing business $15 to $20 billion in workers' compensation costs annually.

WMSDs occur where there is a mismatch between physical requirements of a job and the physical capacity of the worker. Prolonged exposure to ergonomic risk factors such as force, repetition, static postures, awkward postures and vibration particularly in combination or at high levels is likely to cause or contribute to an MSD.

Dental hygiene procedures, for example, frequently require dental hygienists to maintain pinch grasps on small diameter instruments and use repetitive motions with applied force for scaling and root planing. This leads to stress of the thumb joint, wrist and forearm tendons.

It is, therefore, the primary object of the present invention to provide an apparatus that decreases work-related musculoskeletal disorders of the upper extremities.

Another important object of the present invention is to provide an apparatus that decreases fatigue of nerves, muscles, tendons and joints of the upper extremities.

Still another important object of the present invention is to provide an apparatus as aforesaid, which decreases transfer of vibrations from ultrasonic equipment to the upper extremities.

Yet another important object of the present invention is to provide an apparatus as aforesaid, which encourages better posture.

A further important object of the present invention is to provide an apparatus as aforesaid that can be integrated into and used with existing equipment, instruments and tools.

Still another important object of the present invention is to provide an apparatus as aforesaid, which increases patient comfort during a dental hygiene procedure.

Yet another important object of the present invention is to provide an apparatus as aforesaid, which allows a dental hygienist the option of using a palm grasp instead of a pinch grasp.

Another important object of the present invention is to provide an apparatus as aforesaid, which increase the grip size of a tool or instrument to a natural grip size without compromising an operator's or technician's ability to maintain control of the tool or instrument while using fine motor skills.

Still a further object of the present invention is to provide an apparatus as aforesaid, which may be used in a plurality of cross-sectional sizes to vary the technician's grip size to reduce musculoskeletal disorders due to repetitive hand-intensive tasks.

These and other objects of the invention are achieved by a removeable replaceable handle grip for small diameter tools, instruments and equipment that consist of one or more compressible materials such as closed cell rubber with an outer diameter in the range of approximately 0.5 inch to 2.5 inches.

DETAILED DESCRIPTION

Figure 1:
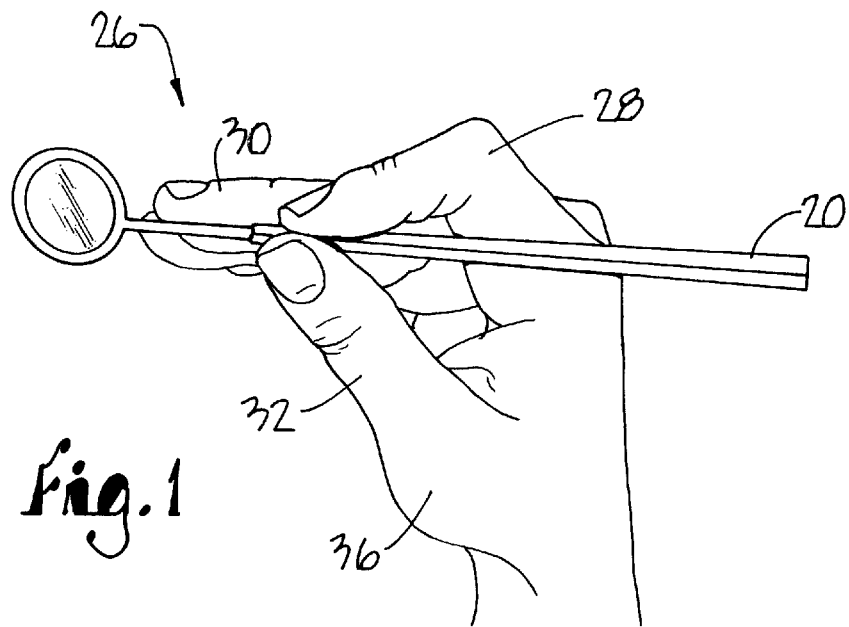
FIG. 1 is an illustration of a right hand holding a dental mirror using a modified pen or pinch grasp.
Figure 2:
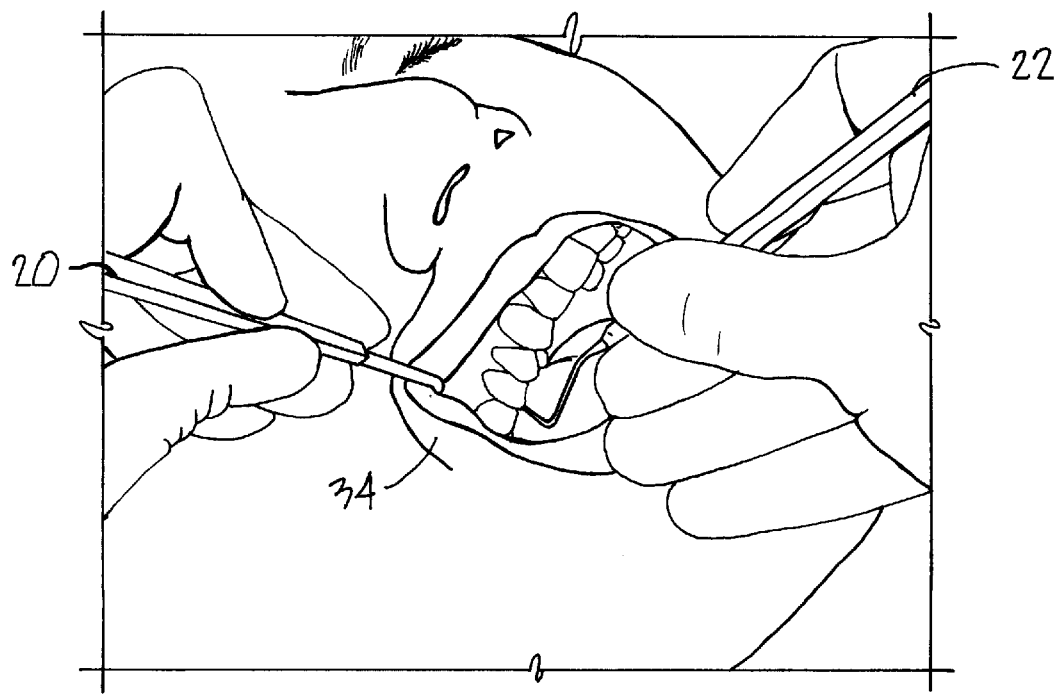
FIG. 2 is an illustration of the mirror in the dental hygienist's left hand retracting the patient's buccal muscosa and a probe in the dental hygienist's right hand probing a maxillary right posterior tooth.

Referring more particularly to the drawings in FIGS. 1–2 the modified pen grip and use of a dental mirror 20 and a curet 22 are illustrated. A modified pen or pinch grip generally indicated by reference number 26 places stress on a technician's index finger and joints 28, middle finger and joints 30 and thumb and joints 32. Because of the relatively small diameter of instruments 20 and 22, and the muscle and tendon force required to retract the patient's buccal mucosa 34 with the dental mirror 20, a tremendous amount of pressure is transferred to the basal or carpometacarpal joint 36 of the thumb 32.

The thumb 32 is considered to be the most important single digit in the hand. One pound of pinch force between the thumb 32 and index finger 28 will produce six to nine pounds of pressure at the basal joint 36 of the thumb 32. Disruptions in the joint 36 surface or the support ligaments can lead to subluxation (slipping of the joint) as well as pain and swelling.

Because of the nature of clinical work places, dental hygienists are at risk of acquiring musculoskeletal disorders (MSD) resulting from the long-term effects of repetitive motion, exposure to vibration, and mechanical stress. These types of MSDs are generally referred to as cumulative trauma disorders (CTDs). MSDs affecting the upper extremities may be caused by grasping small diameter instruments for extended periods of time, having pain or compromised posture during patient care, and frequent exposure to handpiece or ultrasonic scaler vibration. Other factors that contribute to CTDs include the work load on small muscles, tendons and ligaments of the fingers, thumb and hand, and the flexion and extension positions of the wrist during repetitive scaling and polishing.

Figure 3:
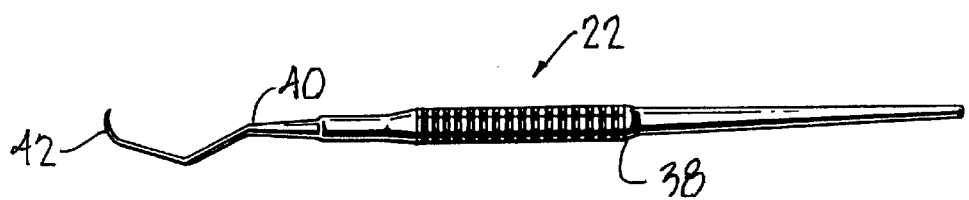
FIG. 3 is a side elevational view of a dental curet illustrating the basic parts of a dental hand instrument.

Generally all dental instruments and as shown in FIG. 3, dental curet 22 includes a handle 38, a shank 40, and a working end 42. Instrument handles 38 are generally thin with a circular cross-section. Handles 38 may have slight modifications in shape and surface texture. The shank 40 of an instrument 22 is thinner than handle 38 and joins the working end 42 of instrument 22 to handle 38. The length and shape of shank 40 varies depending on the type and purpose of the instrument. The design of working end 42 indicates the use of the instrument 22 and determines its classification.

Figure 4:
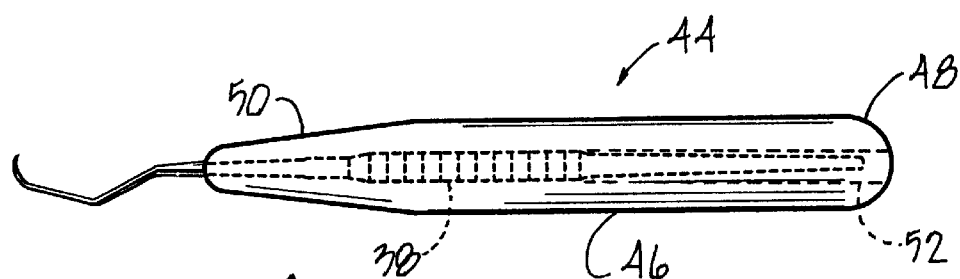
FIG. 4 is a side elevational view of the instrument shown in FIG. 2 with an ergonomic handle of the present invention mounted thereon.
Figure 5:
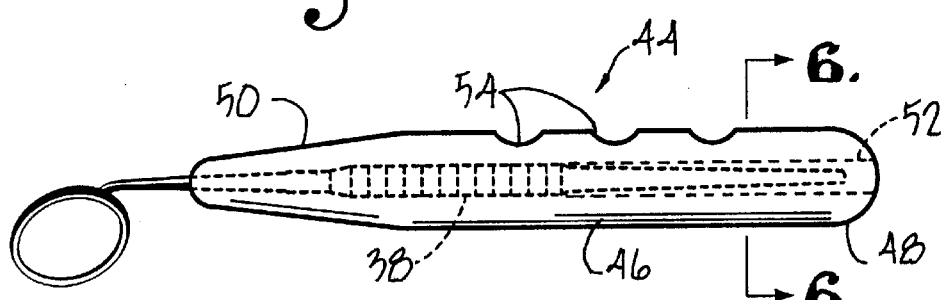
FIG. 5 is a side elevational view of a dental mirror with a first alternatinve embodiment of the ergonomic handle of FIG. 4 mounted thereon.
Figure 6:
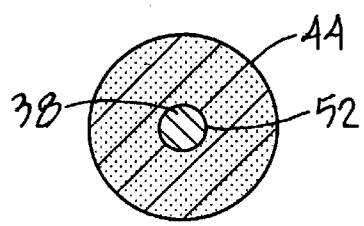
FIG. 6 is a cross-sectional view taken substantially along line 6—6 of FIG. 5.
Figure 7:
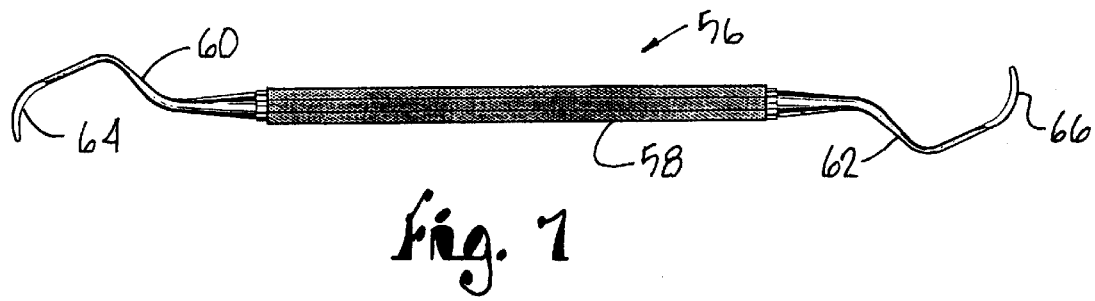
FIG. 7 is a side elevational view of a double-ended Gracey curet.
Figure 8:
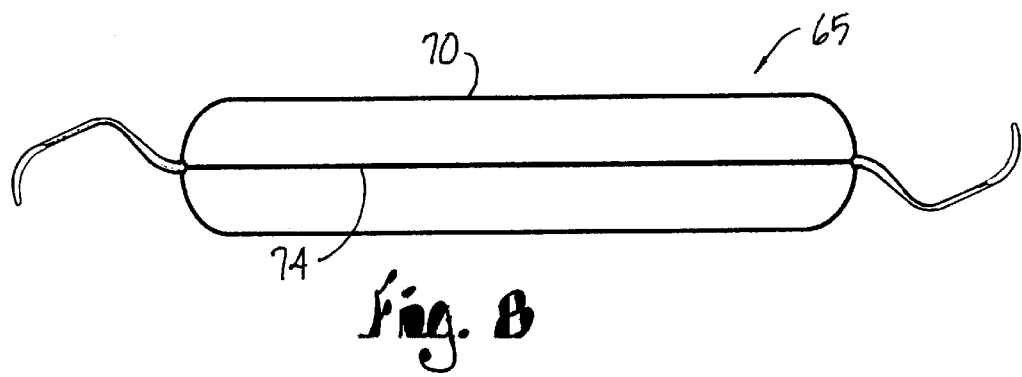
FIG. 8 is a side elevational view of the instrument shown in FIG. 7 with a second embodiment of the ergonomic handle of the present invention mounted thereon.

Referring to FIGS. 4–6, ergonomic handle 44 includes an elongated body member 46, a rounded or blunt end 48, a tapered end portion 50 and an aperture 52 which is sized to accept and secure instrument handle 38. Ergonomic handle 44 preferably has a cylindrical cross-sectional configuration. Typically the outer diameter of ergonomic handle 44 is approximately 0.5 inch to 1.5 inches with an inner diameter an aperture 52 of 0.125 inch to 1.0 inch depending on the diameter of the instrument handle 38. The larger grip size allows the technician to use a natural grip with decreased pressure while using their fine motor skills to maintain control of the instrument 22. Additionally, the technician may use a palm grip for retraction for example.

Tapered end portion 50 extends over a portion of shank 40 and provides better tactile control of instrument 22 by the technician. Tapered end portion 50 also provides increased comfort for the patient when undergoing procedures in which the shank 40 of instrument 22 comes into contact with the patient's mouth such as retracting the patient's buccal mucosa 34 with dental mirror 20 (see FIG. 2), due to the larger outer diameter of taper 50 and the softer material used for ergonomic handle 44.

Ergonomic handle 44 may also include one or more formed grooves 54 in elongated member 46 to enhance gripping by allowing the technician to place his or her fingers in grooves 54.

Referring to FIGS. 7–10, double-ended Gracey curet 56 includes an elongated handle 58 separating spaced-apart shanks 60 and 62 and working ends 64 and 66. Because of the difficulty of sliding an ergonomic handle over either working end or shank, an alternate embodiment of ergonomic handle 68 may be used. Ergonomic handle 68 includes an elongated member 70 which is generally cylindrically shaped, a generally axially aligned aperture 72 extending along the longitudinal axis of elongated member 70 and a channel 74 extending generally radially from the outer surface of member 70 to aperture 72. Channel 74 may be separated to allow insertion of handle 58 into aperture 72. Aperture 72 may have a contact adhesive along its circumferential surface to securely hold handle 58 in place.

Figure 9:
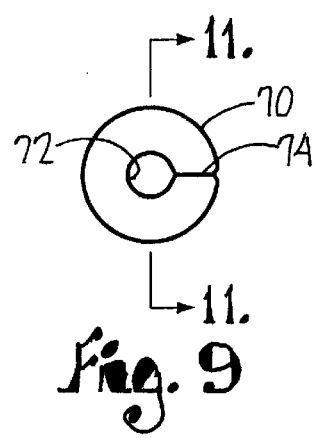
FIG. 9 is an end view of the ergonomic handle of FIG. 8.
Figure 10:
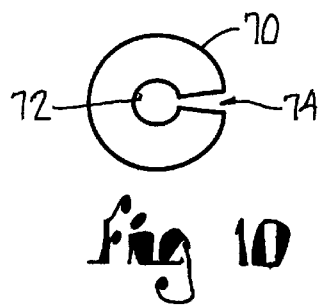
FIG. 10 is an end view of the ergonomic handle of FIG. 8.
Figure 11:
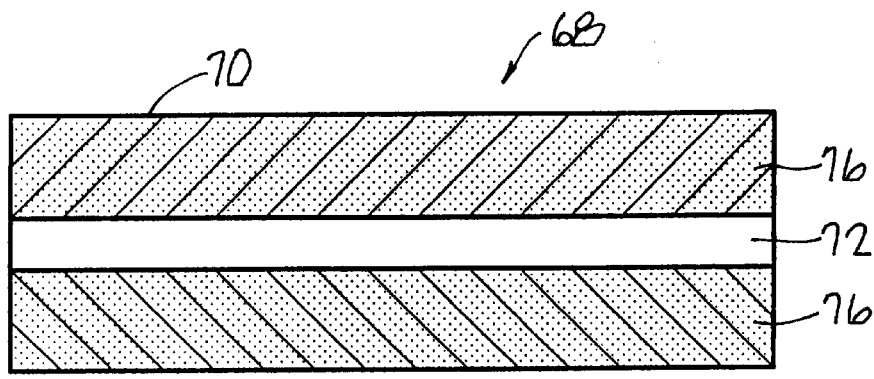
FIG. 11 is a cross-sectional view taken substantially along line 11—11 of FIG. 9.
Figure 12:
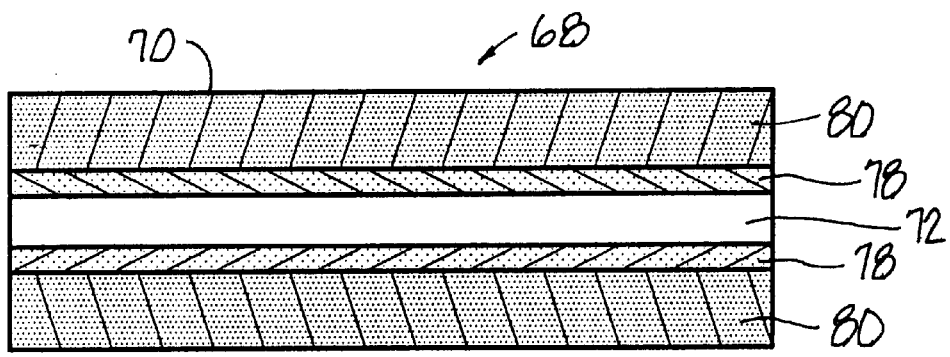
FIG. 12 is dual-layer embodiment of FIG. 11.
Figure 13:
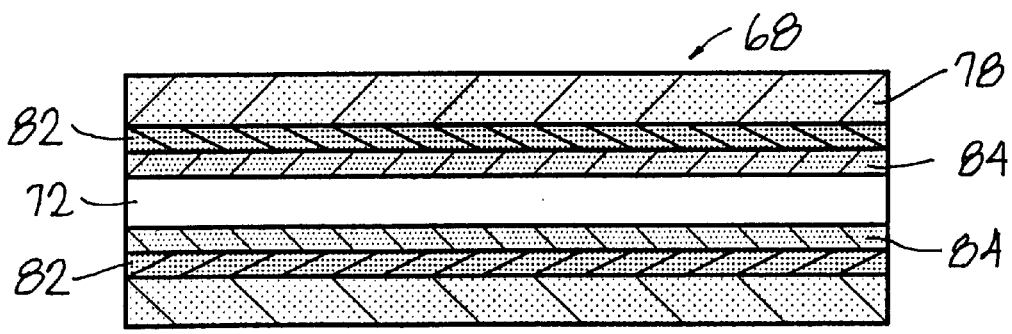
FIG. 13 is tri-layer embodiment of FIG. 11.

A cross-sectional view of ergonomic handle 68 along line 11—11 of FIG. 9 is shown in FIG. 11 with alternate embodiments shown in FIGS. 12 and 13. In the preferred embodiment, ergonomic handle 68 is formed from a single closed cell rubber or silicone material 76. One such material is a neoprene closed cell rubber with a density of approximately 8–12 pounds/cubic foot, a compression deflection of 2–5 pounds/square inch, and a shore hardness value of approximately 25–45. Other rubbers such as polyethylene, ethylene propylene terpolymer (EPT), ethylene vinyl acetate (EVA) and nitvile (NBR) may be used. These rubbers are available from Rubatex Corporation, stock number R-421-N (neoprene). Generally the outer layer 76 is readily deformable.

In general, ergonomic handle 68 may be made from a material with a density in the range from 2 to 30 p.c.f, a compression deflection in the range from approximately 2 to 20 p.s.i. and a shore hardness value in the range of 20–80. Generally, the softer the material, the more comfortable the grip and the better the material absorbs vibrations. However, a material that is too soft does not provide the technician with sufficient tactile sensitivity to effectively use some instruments.

Referring to FIG. 12, a dual laminate ergonomic handle 68 is illustrated using a generally softer material 78 surrounding aperture 72, which is secured to a relatively harder material 80 using a contact adhesive bond. Material 78 may consist of a rubber such as ETP with a density from 2–5 pcf (Rubatex stock number R-4911-T). Material 80 may consist of a firmer rubber neoprene with a density of 15–30 pcf (Rubatex stock number G-207-N). Using a dual laminate system high frequency vibrations from instruments such as ultrasonic cleaners may be significantly reduced by material 78 while material 80 provides the operator with a comfortable yet firm grip. Alternatively, ergonomic handle 68 may be formed in a flat sheet that may be wrapped around handle 58 to form elongated member 70, and may be releaseably secured with a contact adhesive or with one or more bands.

Referring to FIG. 13, a tri-laminate ergonomic handle 68 is illustrated using a top later 78 of soft rubber such as EPT with a density of approximately 3 pcf, a middle layer 82 of a relatively firm rubber such as a neoprene with a density of 22–35, a compression deflection of 17–24 p.s.i. and a shore hardness of 70–85, and a third layer 84 of an intermediate firmness rubber such as nitrile with a density of 9–18 p.c.c. and a shore hardness of 40–60. A three layer system may be used to suppress a wide range of vibration frequencies. It should be understood that a plurality of layers may be used to tailor ergonomic handle 68 to a specific need.

In a dental office application, ergonomic handle 44 and 68 (FIGS. 4 and 8) may be made of a high-temperature silicone rubber or rubber laminate which is autoclaveable. A closed cell rubber with a finished surface may also be used to prevent biocontaminants from becoming trapped in the rubber cells. However, due to the intolerance of most rubbers such as neoprene to high temperatures used in autoclaves, ergonomic handles 44 and 68 may be disposable.

Although the present invention has been disclosed with reference to periodontal instruments, and periodontal procedures, it is understood that the ergonomic handle of the present invention may be adapted to any shaped tool or instrument handle.

It is to be understood that while certain forms of this invention have been illustrated and described, it is not limited thereto except insofar as such limitations are included in the following claims and equivalents thereof.

Having thus described the invention, what is claimed as new and desired to be secured by Letters Patent is follows:

1. In combination with a periodontal instrument having a handle portion and a working end portion, a removable ergonomic grip comprising:

an elongated body member having a gripping surface, a pair of spaced-apart ends and a longitudinally extending internal aperture;

said aperture receiving the handle portion of said periodontal instrument;

a channel extending longitudinally from said first end to said second end and radially from said gripping surface to said aperture; and a contact adhesive along a circumference of said aperture;

said body member comprising an elastomer having a shore hardness value in a range from approximately 20 to 80, and a cross-sectional diameter of approximately 0.5 inch to 2 inches.

2. The ergonomic grip as claimed in claim 1, wherein said end adjacent said working end portion of said instrument being tapered.

3. The ergonomic grip as claimed in claim 1, wherein said end opposite said working end portion being rounded.

4. The ergonomic grip as claimed in claim 1, wherein said elastomer has a density ranging from 5 to 12 pounds per cubic foot.

5. The ergonomic grip as claimed in claim 1, wherein said elastomer has a density ranging from approximately 12 to 20 pounds per cubic foot.

6. The ergonomic grip as claimed in claim 1, wherein said elastomer has a density ranging from approximately 20 to 35 pounds.

7. The ergonomic grip as claimed in claim 1, wherein said elastomer comprises a silicone rubber.

8. In combination with a periodontal instrument having a handle portion and at least one working end portion, a removable ergonomic grip comprising:

an elongated body member having a gripping surface, a pair of spaced-apart ends, and a longitudinally extending internal aperture, said aperture receiving the handle portion of said periodontal instrument;

said body member having a cross-sectional diameter ranging from approximately 0.5 inch to 2 inches and comprising a first elastomer layer and a second elastomer layer having different shore hardness values.

9. The ergonomic grip as claimed in claim 8, wherein said end adjacent said working end portion of said instrument being tapered.

10. The ergonomic grip as claimed in claim 8, wherein said instrument having a pair of working end portions and wherein each of said ends adjacent said working end portions of said instrument being tapered.

11. The ergonomic grip as claimed in claim 8, wherein said first elastomeric layer has a shore hardness value ranging from approximately 40 to 80 and said second elastomeric layer has a shore hardness value ranging from approximately 20 to 40.

12. The ergonomic grip as claimed in claim 11, wherein said first elastomeric layer being the outer layer.

13. The ergonomic grip as claimed in claim 11, wherein said first elastomeric layer being the inner layer.

14. The ergonomic grip as claimed in claim 8, wherein said first elastomeric layer has a density ranging from approximately 5 to 12 pounds per cubic foot and said second elastomeric layer has a density ranging from approximately 12 to 35 pounds per cubic foot.

15. The ergonomic grip as claimed in claim 8, wherein said first elastomeric layer has a density less than the density of said second elastomeric layer.

16. The ergonomic grip as claimed in claim 8, wherein said first layer is secured to said second layer.

17. The ergonomic grip as claimed in claim 8, further comprising a third elastomeric layer between said first and second layers.

18. The ergonomic grip as claimed in claim 8, wherein at least one of said elastomeric layers has a different shore hardness value.

19. The ergonomic grip as claimed in claim 8, wherein at least one of said elastomeric layers has a different density.

20. The ergonomic grip as claimed in claim 8, further comprising a plurality of elastomeric layers between said first and second layers.

21. A removable ergonomic grip for an elongated instrument handle comprising:

an elastomeric sheet having first and second surfaces and a plurality of layers having shore hardness values ranging from approximately 20 to 80, a first open configuration, and a second closed configuration, whereby said sheet being adapted to wrap around said instrument handle in said second closed position with said first surface adjacent said instrument handle, said second surface forming an exterior gripping surface, and having a cross-sectional diameter ranging from approximately 0.5 to 2 inches in said second closed position.

22. The ergonomic grip as claimed in claim 21, wherein said elastomeric sheet has a density ranging from 5 to 12 pounds per cubic foot.

23. The ergonomic grip as claimed in claim 21, wherein said elastomeric sheet has a density ranging from approximately 12 to 20 pounds per cubic foot.

24. The ergonomic grip as claimed in claim 21, wherein said elastomeric sheet has a density ranging from approximately 20 to 35 pounds.

25. The ergonomic grip as claimed in claim 21, wherein said elastomeric sheet comprises a silicone rubber.

26. The ergonomic grip as claimed in claim 21, further comprising a contact adhesive between said first surface and said instrument handle for releaseably securing said sheet to said instrument handle.

* * * * *